United States Patent [19]

Benejean et al.

[11] Patent Number: 5,853,735
[45] Date of Patent: Dec. 29, 1998

[54] AVIRULENT ANTI-RABIES VACCINE

[75] Inventors: Jacqueline Benejean, Chilly Mazarin; Anne Flamand, Gif Sur Yvette; Marie-Christine Tuffereau, Paris; Patrice Coulon, Palaiseau; Florence Lafay, Versailles, all of France

[73] Assignee: Virbac, France

[21] Appl. No.: 785,616

[22] Filed: Jan. 17, 1997

Related U.S. Application Data

[63] Continuation of Ser. No. 95,163, Jul. 20, 1993, abandoned.

[30] Foreign Application Priority Data

Jul. 20, 1992 [FR] France ................................. 92 08947

[51] Int. Cl.$^6$ .............................. C12N 15/00; C12P 21/06; A61K 39/21; A61K 39/205
[52] U.S. Cl. .................................. 424/208.1; 424/204.1; 424/184.1; 424/224.1; 435/172.1; 435/173.1; 435/69.1; 435/239
[58] Field of Search .............................. 424/184.1, 204.1, 424/224.1, 208.1; 435/172.1, 173.1, 69.1, 239

[56] References Cited

FOREIGN PATENT DOCUMENTS

| 0 350 398 | 7/1989 | European Pat. Off. |
|---|---|---|
| 0350398 | 1/1990 | European Pat. Off. ..... A61K 39/205 |

OTHER PUBLICATIONS

Seif, et al, 1985, "Rabies Virulence: Effect on Pathogenicity . . ." J. of Virol. 53(3): 926–934.
Tuffereau, et al, 1889, "Arginine or Lysine in Position 333 . . ." Virology 172:206–212.
Immunochemistry Abstract 105:4059s. "Avirulent Mutants of Rabies Virus . . .".
Coulon, et al, 1982, "Molecular Basis of Rabies Virus Virulence . . ." J. Gen. Virol. 61:97–100.
Tidke, et al, 1987, "Characterization of a Double Avirulent Mutant . . ." Vaccine 5(3):229–233.
Pepin et al., Ann. Inst. Pasteur Virol 136(1), 1985.
Yelverton et al., Science vol. 219, p. 614, 1983.
Tidke et al., Vaccine 5 (3), 1987, pp. 229–233.
P. Coulon et al., J. Gen. Virol., vol. 61, pp. 97–100, 1982.
15–Immunochemistry Abstract, vol. 106, 1986, 105:4059s Avirulent Mutants of Rabies Virus: Change in the Site III of the Glycoprotein.
3–Biochem. Genetics, vol. 102, 1985, 102:143960y Rabies Virulence: Effect on Pathogenicity and Sequence Characterization of Rabies Virus Mutations Affecting Antigenic Site III of the Glycoprotein.
Virology, vol. 172, 1989, New York, USA, pp. 206–212, Tuffereau et al., "Arginine of Lysine in Position 333 of Era and CVS Glycoprotein is Necessary for Rabies Virulence in Adult Mice".
Proceedings of the National Academy of Sciences, USA, vol. 80, 1983, Washington, D.C., USA, pp. 70–74, Dietzschold et al., "Characterization of an Antigenic Determinant of the Glycoprotein that Correlates with Pathogenicity of Rabies Virus".

*Primary Examiner*—Lynette F. Smith
*Attorney, Agent, or Firm*—Nawrocki, Rooney & Sivertson, P.A.

[57] ABSTRACT

The invention relates to an avirulent anti-rabies vaccine which consists of an avirulent mutant of an SAD strain of the rabies virus, the glycoprotein of which possesses in position 333 a naturally occurring amino acid whose codon differs from those of arginine by at least two nucleotides.

7 Claims, 3 Drawing Sheets

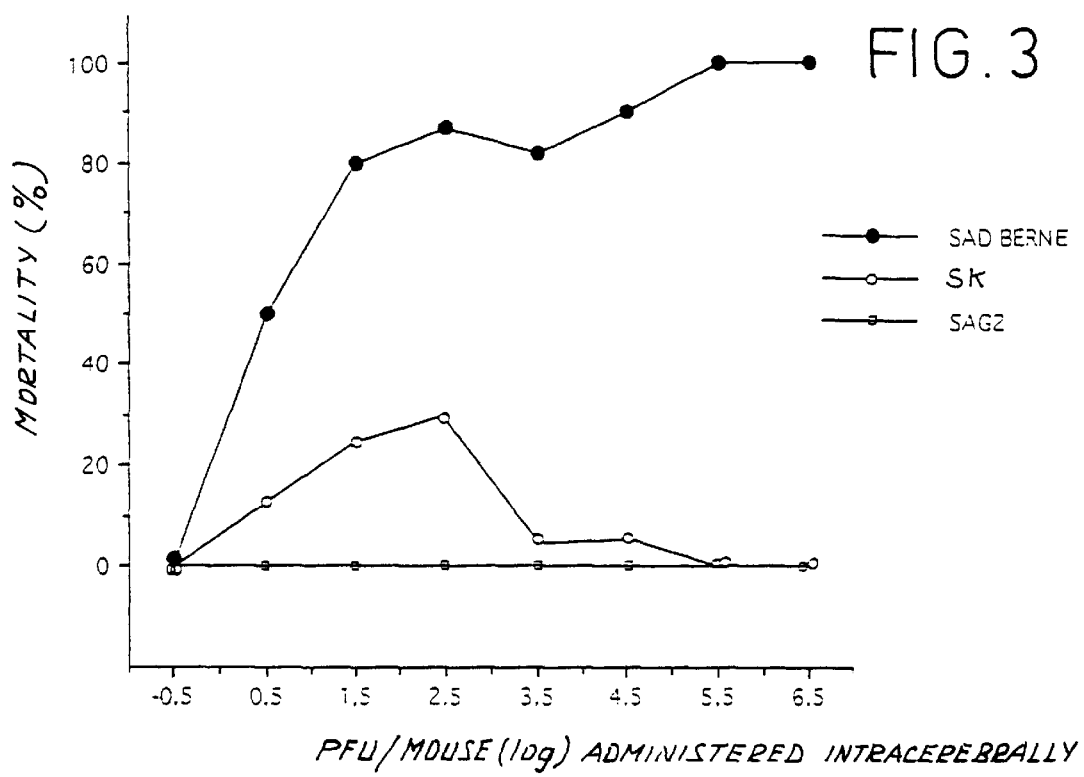
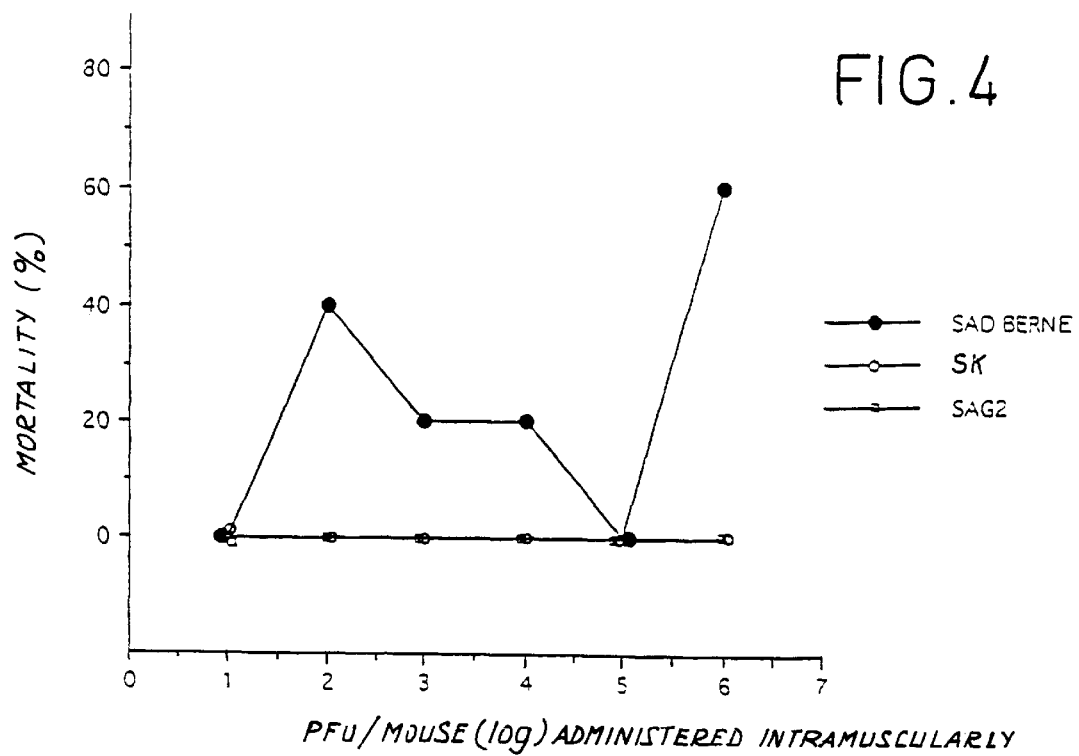

AVIRULENT ANTI-RABIES VACCINE

This application is a continuation of U.S. Ser. No. 08/095,163 filed Jul. 20, 1993, now abandoned.

The present invention relates to a novel anti-rabies vaccine.

The rabies virus is a rhabdovirus consisting of five proteins, including one external protein, namely the glycoprotein, which triggers the synthesis of neutralizing antibodies in inoculated animals. Injection of the purified glycoprotein protects the animal against superinfection. The strains of rabies virus most commonly used, especially the CVS strain and the ERA strain, from which are derived the SAD strains such as the SAD Berne and SAD B19 strains, are described in "Rabies Viruses" by H. F. Clark and T. J. Wiktor—Strains of Human Viruses, published by Majer and Plotkin Karger, Basle, 1972, pp. 177–182. The amino acid sequence of the glycoprotein of the CVS strain has been described by Yelverton et al. in "Rabies virus glycoprotein analogs: biosynthesis in *Escherichia coli*", Science, 219, 614–620.

This glycoprotein has two distinct major antigenic sites associated with the neutralization of the virus (sites II and III). Site III in position 330–340 contains arginine 333, which determines the virulence of this strain.

The amino acid sequence of the glycoprotein of the SAD Berne strain has not been completely established. However, it has been possible to determine that antigenic site III of the glycoprotein of the SAD Berne strain is identical to that of the glycoprotein of the CVS strain.

The anti-rabies vaccines in current use are either vaccines produced from inactivated viruses, or vaccines consisting of viral strains whose virulence has been attenuated, or recombinant viruses (for example the vaccine).

The viruses can be inactivated by a variety of methods, especially by chemical methods such as treatment with formaldehyde or β-propiolactone.

The major disadvantage of this vaccine production method is the handling of virulent strains, which requires very strict operating conditions and carries risks of contamination of the personnel involved.

Moreover, the inactivated vaccines administered orally have no protective power.

Attenuation of the virulence of viral strains is a well-known technique; it can be carried out for example by successive passes of the viral strains over a host which is different from the vector species (rabbit or mouse, for example), or in cell cultures. This gives strains which are poorly adapted to the original host and are therefore less pathogenic towards the latter while at the same time retaining their vaccinating capacity.

The SAD strains, such as the SAD B19 and SAD Berne strains, which are in the public domain, are attenuated strains which have already been tested in Europe for the vaccination of foxes. They can be mixed with bait for oral administration. However, these strains have been shown to be pathogenic towards other animal species and humans. There is therefore a potential risk of contamination, which considerably reduces the value of these strains for oral vaccination.

In fact, for example, the oral administration of the SAD Berne strain to a group of 23 wild rodents selected from *Apodemus flavicolus* and *sylvaticus, Arvicola terrestris, Clethrionomys clareolus* and *Minotus agresti* caused the death of two animals by rabies.

Tests on mice have also shown that the SAD Berne strain is pathogenic towards this species, both by intracerebral administration and by intramuscular administration, as shown by the curves of the attached FIGS. 1a and 1b.

BRIEF DESCRIPTION OF THE FIGURES

FIG. 3 is a graph giving the % mortality (on the ordinate) as a function of the amount of mutant injected per mouse (on the abscissa).

FIG. 4 gives the % mortality (on the ordinate) as a function of the dose administered in PFU/mouse (on the abscissa).

Figure 1A:
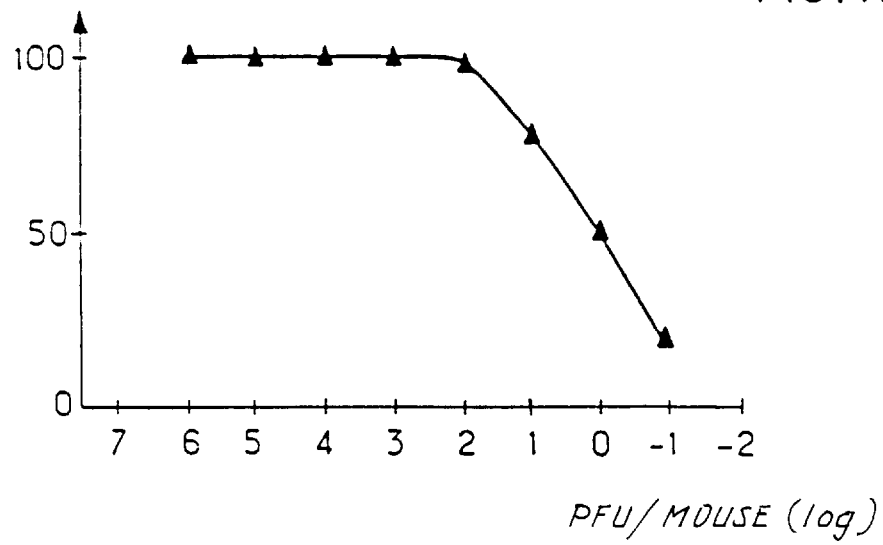
FIG. 1a is the mortality curve for adult mice as a function of the doses (in plaque-forming units) administered intracerebrally.
Figure 1B:
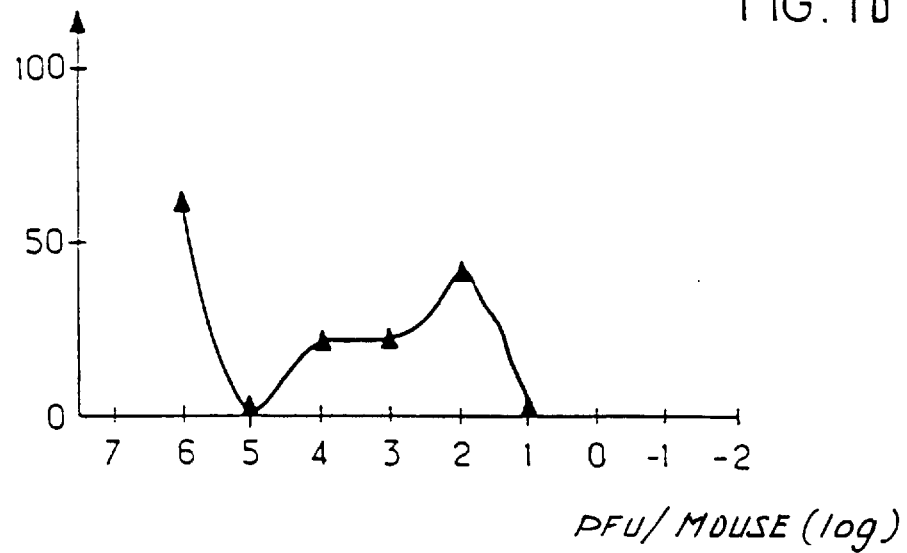
FIG. 1b is the mortality curve for adult mice as a function of the doses (in plaque-forming units) administered intramuscularly.

A mortality of 10% was observed in mice at a dose of $10^{5.5}$ PFU administered orally.

Thus the SAD Berne strain as such is a danger to wildlife and humans if it is used in campaigns for the vaccination of foxes. The same applies to the SAD B19 strain.

An avirulent anti-rabies vaccine has already been proposed in order to mitigate this disadvantage. This vaccine, described in European patent application 350 398, consists of an avirulent mutant of an SAD strain of the rabies virus in which arginine 333 of the glycoprotein has been replaced with an amino acid other than lysine, for example glycine, isoleucine or serine.

This mutant is derived by changing a single nucleotide in the codon of arginine 333.

Unfortunately, this mutant can revert to the parent strain by a simple reverse mutation.

This vaccine, which is used for oral administration, is not therefore totally without danger as regards the other animal species.

The present invention relates to an effective vaccine which enables the above disadvantages to be mitigated.

The vaccine according to the invention consists of an avirulent mutant of an SAD strain of the rabies virus in which arginine 333 of the glycoprotein has been replaced with a naturally occurring amino acid whose codon differs by two nucleotides from those coding for arginine.

The invention further relates to the avirulent mutants of an SAD strain of the rabies virus in which the arginine in position 333 of the glycoprotein has been replaced with an amino acid whose codon differs from those of arginine by two nucleotides.

The invention further relates to a method of obtaining the above-defined avirulent mutants. This method consists in:

1/ selecting, from an SAD strain of the rabies virus, those mutants which are not neutralized by a monoclonal antibody neutralizing said SAD strain but not neutralizing the TAG1 strain defined below;

2/ isolating, by sequencing of the 333 region of the glycoprotein of the mutants selected in step 1/, a mutant which possesses a lysine in position 333;

3/ preparing a monoclonal antibody which neutralizes both said SAD strain and the mutant obtained in step 2/, but does not neutralize the TAG1 strain; and 4/ effecting a second selection from the mutants obtained in step 1/ with the aid of the monoclonal antibody prepared in step 3/.

The monoclonal antibodies used for selecting the mutants according to the invention are obtained by the fusion of myeloma cells with cells producing antiviral antibodies according to the hybridization technique described by KOHLER and MILSTEIN in NATURE, vol. 256, 495–497 (1975), a technique which is now well known to those skilled in the art.

This technique can be used to fuse cells originating from different species; however, it is advantageous to use cells originating from the same animal species. For example, it is preferable to use on the one hand mouse myeloma cells and on the other hand spleen cells of mice previously immunized with a strain of the rabies virus according to the protocol defined below.

In general terms, this hybridization method, described with reference to mouse cells, comprises the following steps:

1) immunization of mice with a given amount of virus inactivated with β-propiolactone;

2) removal of the spleen of the immunized mice and separation of the splenocytes;

3) fusion of the splenocytes thus obtained with mouse myeloma cells in the presence of a fusion promoter;

4) culture of the hybrid cells obtained in a selective medium on which the non-fused myeloma cells do not develop, and in the presence of appropriate components; and 5) selection of the cells producing the desired antibody and cloning of these cells.

The immunization protocol comprises the intraperitoneal injection of Balb-C mice with 100 μg of CV5 virus inactivated with β-propiolactone, together with FREUND's complete adjuvant, and an intravenous booster dose 4 days before fusion after a rest period of 1 month.

The splenocytes of the immunized mice are recovered after removal of the spleen according to the conventional procedure.

The mouse myeloma cells used to obtain the neutralizing monoclonal antibodies are Balb-C mouse myeloma cells originating from the $SP_2O$ line. These myeloma cells were selected for their sensitivity to aminopterin and cultured on an appropriate medium such as Eagle's essential medium modified by DULBECCO (Dulbecco Modified Eagle medium), hereafter referred to as DMEM, to which 15% of foal serum has been added.

The myeloma cells were fused with the splenocytes by mixing $5 \cdot 10^7$ myeloma cells with $5 \cdot 10^7$ spleen cells of immunized mice, in the presence of a fusion promoter such as, for example, a polyethylene glycol.

After incubation at 37° C., the cells are washed in DMEM, resuspended and then cultured on a selective medium appropriate only for growing the hybrid cells. Such a medium contains hypoxanthine, aminopterin and thymidine.

The culture supernatants are then selected, 7 to 20 days after fusion, by bringing the supernatants into contact with a suspension of CVS virus and selecting the antibodies which neutralize said suspension.

"Antibodies neutralizing a virus" are understood as meaning antibodies which, when brought into contact with a suspension of said virus, inhibit the virulence thereof.

The neutralizing power of the monoclonal antibodies obtained above is determined by a conventional method well known to those skilled in the art. This method consists in bringing 100 μl of virus suspension containing 1000 PFU of virus into contact with 100 μl of hybridoma culture supernatant, infecting a cell culture with this mixture and, after 4 days of incubation, counting the lysis plaques under agar by the method described by BUSSEREAU et al., 1982, J. Virol. Méth., vol. 4, pp. 277–282. The antibody is neutralizing if it inhibits all plaque formation under agar under the conditions described above.

Then, of these antibodies, those are selected which do not neutralize the TAG1 avirulent mutant derived from the CVS strain, deposited in the Collection Nationale de Cultures de Micro-organismes (C.N.C.M.) INSTITUT PASTEUR-FRANCE on 12th Apr. 1985 under no. I-433.

The resulting monoclonal antibodies, which therefore neutralize the CVS strain but do not neutralize the TAG1 avirulent mutant, make it possible to select avirulent mutants from any strain of rabies virus which is neutralized by these monoclonal antibodies.

The monoclonal antibodies thus obtained are antibodies which also neutralize the SAD strains of the rabies virus, so they are suitable for effecting the first selection of the method of the invention.

The sequencing of the 333 region of the glycoprotein of the mutants selected in step 1/ is performed by the conventional method well known to those skilled in the art [SANGER et al., 1977, Proc. Nat. Acad. Sci. USA, vol. 74, pp. 5463–5467].

This sequencing makes it possible to isolate a mutant which possesses a lysine in position 333 of the glycoprotein; this mutant is hereafter referred to as "SK mutant".

The codon (AAA) of this amino acid (lysine) differs by a single nucleotide from that of the arginine in position 333 of the SAD strain, the codon of the arginine in position 333 of the SAD strain being AGA.

This is followed by preparation of the monoclonal antibody which neutralizes both the SAD strain and the mutant obtained above.

This monoclonal antibody is obtained by selecting, from the monoclonal antibodies which neutralize the SAD strain and do not neutralize TAG1, that monoclonal antibody which also neutralizes the lysine mutant or SK mutant obtained above.

This monoclonal antibody then makes it possible to effect the second selection (step 4) of the method of the invention.

The pathogenic potency of the mutants resulting from this second selection is then tested by the intracerebral injection of adult mice with $10^5$ PFU. The mutants which do not kill at this dose and by this injection route are considered to be avirulent.

The mutants according to the invention are double avirulent mutants of an SAD strain, such as the SAD Berne strain in particular, resulting from two successive selections with the aid of the above-defined monoclonal antibodies.

The mutants according to the invention can also contain other mutations, for example a mutation conferring resistance to a monoclonal antibody specific for antigenic site II, which allows the recognition of a possible virulence revertant of the SAD strains used for the oral vaccination of foxes.

The mutants according to the invention can be multiplied on BHK 21 baby hamster kidney cells in the presence of GEM (minimum essential medium modified by Glasgow, marketed by FLOW) and 2% of calf serum, at 33° C. and in a moist atmosphere containing 5% of $CO_2$.

They are titrated by the usual methods, for example by determining the 50% lethal dose ($LD_{50}$) in young mice, by immunofluorescence or counting of the lysis plates under agar. They can be stored at −70° C.

Analysis of the nucleotide sequence of the glycoprotein of these mutants has shown that the codon of the amino acid in position 333 differs by at least two nucleotides from all the possible codons of arginine. Of the mutants which satisfy this condition, the mutant which possesses a glutamic acid in position 333 is very particularly preferred because it multiplies well in cell culture, it is less pathogenic towards newborn mice and it has a good protective power.

The double mutant carrying a glutamic acid whose codon is GAA in place of the arginine in position 333, obtained by the above method from the SAD Berne strain and referred to hereafter as SAG2, was deposited in the Collection Nationale de Cultures de Microorganismes (C.N.C.M.) INSTITUT PASTUER-FRANCE on 9th Jul. 1992 under no. I-1238. This mutant contains another mutation, namely resistance to a monoclonal antibody specific for antigenic site II, which serves as an additional marker of the strain.

The invention will now be described in greater detail with reference to the SAG2 mutant, without thereby limiting the scope of the invention to this mutant alone.

A—Tests for Genetic Stability of the Strain During Passes in Young Mouse Brains Six 4-day-old mice were injected with $10^3$ PFU of SAG2. When the animals had become ill (D6), they were sacrificed. Six individual ground preparations were made up; each ground preparation was titrated and 3 adult mice (pathogenicity control) and one young mouse (next pass) were injected with 30 µl of a 1/10 dilution. The 6 young mice thus made it possible to carry out 6 independent series of 3 passes.

The titers of the brains in PFU/ml are given in the Table below:

| Series | A | B | C | D | E | F |
| --- | --- | --- | --- | --- | --- | --- |
| 1st pass | $>5 \cdot 10^7$ | $1.5 \cdot 10^7$ | $10^7$ | $10^6$ | $10^6$ | $10^6$ |
| 2nd pass | $>5 \cdot 10^7$ | $2.5 \cdot 10^7$ | $>5 \cdot 10^7$ | $>5 \cdot 10^7$ | $>5 \cdot 10^7$ | $>5 \cdot 10^7$ |
| 3rd pass | $>5 \cdot 10^7$ | $>5 \cdot 10^7$ | $>5 \cdot 10^7$ | $>5 \cdot 10^7$ | $>5 \cdot 10^7$ | $>5 \cdot 10^7$ |

All the adults (i.e. 54 mice) injected after the 1st, 2nd or 3rd pass survived, showing the absence of reversion.

B—Protective Power of SAG2

Mice were injected intracerebrally with the SAG2 mutant and the protective power of this mutant was determined by intramuscular testing of 100 $LD_{50}$ of the CVS strain.

Figure 2:
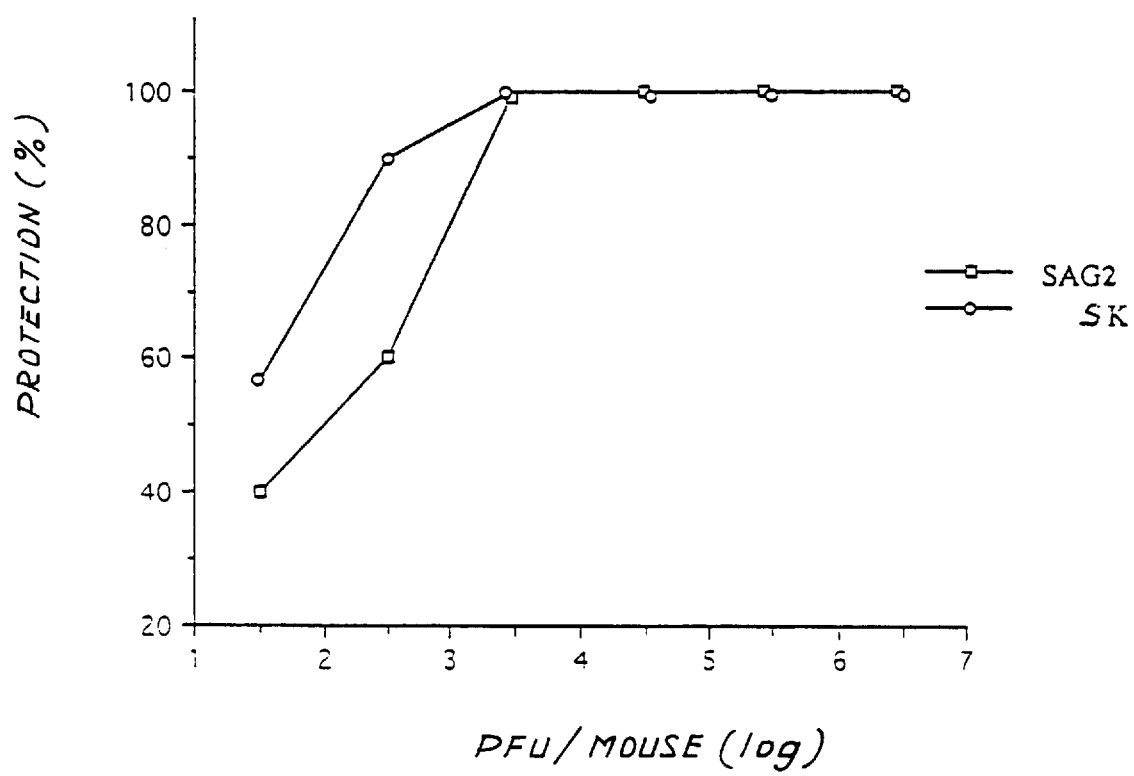
FIG. 2 is a graph giving the protective power (%) on the ordinate as a function of the amount of mutant injected, expressed in PFU/mouse (log).

The results obtained are shown in FIG. 2, which is a graph giving the protective power (%) on the ordinate as a function of the amount of mutant injected, expressed in PFU/mouse (log). The same test was repeated with the SK mutant possessing a lysine in position 333.

The protective power of SK and SAG2 was found to be 100% at $10^4$ PFU/mouse and above.

C—Pathogenicity of SAG2 by Intracerebral Administration

Mice were injected with the SAG2 mutant at doses ranging from $10^{-0.5}$ to $10^6$ PFU/mouse and no mortality was observed over a 28-day period.

In parallel, the same experiment was performed with the SAD BERNE virus or the SK mutant.

The results are shown in FIG. 3, which is a graph giving the % mortality (on the ordinate) as a function of the amount of mutant injected per mouse (on the abscissa).

It is found that the SAG2 mutant causes no mortality, whereas the SK mutant has a weak residual pathogenic potency.

D—Pathogenicity of SAG2 by Intramuscular Administration

The above test was repeated except that administration was intramuscular. The results obtained are shown in FIG. 4, which gives the % mortality (on the ordinate) as a function of the dose administered in PFU/mouse (on the abscissa).

It is seen that SAG2 and the SK mutant cause no mortality.

The mutants according to the invention can be administered as a live vaccine by any of the modes of administration normally used for vaccination, and especially by intramuscular or oral administration. The mutants are advantageously diluted in a pharmaceutically acceptable, inert vehicle such as isotonic solution.

What is claimed is:

1. An isolated double avirulent mutant of the SAD Berne strain of rabies virus, deposited in the Collection Nationale de Cultures de Micro-organismes (C.N.C.M.)-INSTITUT PASTEUR-FRANCE on 9th Jul. 1992 under no. I-1238, said mutant having in position 333 glutamic acid, whose codon differs from all codons of arginine by at least two nucleotides.

2. A method of obtaining the double base mutants according to claim 1, which comprises the steps of:
   a) contacting a SAD strain of rabies virus with a first monoclonal antibody which neutralizes said SAD strain but does not neutralize the TAG1 strain of rabies virus, which TAG1 strain is deposited under n°-I-433 in Collection Nationale de Cultures de Microorganismes;
   b) selecting from said SAD strain of rabies virus, those mutants not neutralized by said first monoclonal antibody;
   c) nucleotide-sequencing amino acid position 333 of the glycoprotein of said SAD mutants selected in step b;
   d) isolating, from said SAD mutants nucleotide-sequenced in step c, those SAD mutants which possess a lysine in position 333;
   e) preparing a second monoclonal antibody which neutralizes both the SAD strain and SAD mutants isolated in step b, but does not neutralize the said TAG1 strain; and
   f) selecting from said SAD mutants selected in step b, those mutants which are not neutralized by said second monoclonal antibody.

3. An isolated avirulent anti-rabies vaccine which consists of an avirulent double base mutant of a SAD strain of the rabies virus, the glycoprotein of which possesses in position 333 a naturally occurring amino acid whose codon differs from all codons of arginine by at least two nucleotides; wherein said avirulent double base mutant is obtained from the process comprising the steps of:
   a) contacting a SAD strain of rabies virus with a first monoclonal antibody which neutralizes said SAD strain but does not neutralize the TAG1 strain of rabies virus, which TAG1 strain is deposited under n°-I-433 in Collection Nationale de Cultures de Microorganismes;
   b) selecting from said SAD strain of rabies virus, those mutants not neutralized by said first monoclonal antibody;
   c) nucleotide-sequencing amino acid position 333 of the glycoprotein of said SAD mutants selected in step b;

d) isolating, from said SAD mutants, nucleotide-sequenced in step c, those SAD mutants which possess a lysine in position 333;

e) preparing a second monoclonal antibody which neutralizes both the said SAD strain and mutants isolated in step d, but does not neutralize the said TAG1 strain; and f) selecting from said SAD mutants selected in step b, those mutants which are not neutralized by said second monoclonal antibody.

4. A vaccine according to claim 3 wherein the amino acid in position 333 is glutamic acid.

5. A method of obtaining an isolated double base mutant avirulent anti-rabies vaccine possessing in position 333 an amino acid whose codon differs from all codons of arginine by at least two nucleotides, which comprises the steps of:

a) contacting a SAD strain of rabies virus with a first monoclonal antibody which neutralizes said SAD strain but does not neutralize the TAG1 strain of rabies virus, which TAG1 strain is deposited under n°-I-433 in Collection Nationale de Cultures de Microorganismes;

b) selecting from said SAD strain of rabies virus, those mutants not neutralized by said first monoclonal antibody;

c) nucleotide-sequencing amino acid position 333 of the glycoprotein of said SAD mutants selected in step b;

d) isolating, from said SAD mutants nucleotide-sequenced in step c, those SAD mutants which possess a lysine in position 333;

e) preparing a second monoclonal antibody which neutralizes both the SAD strain and SAD mutants isolated in step d, but does not neutralize the said TAG1 strain; and f) selecting from said SAD mutants selected in step b, those mutants which are not neutralized by said second monoclonal antibody.

6. A vaccine according to claim 3, wherein the mutant is a mutant of the SAD Berne strain.

7. A vaccine according to claim 6, wherein the mutant is the mutant deposited in the Collection Nationale de Cultures de Microorganismes C.N.C.M.-Institut PASTEUR-France, on 9th July 1992 under n° I-1238, said mutant having in position 333 glutamic acid, whose codon differs from all codons of arginine by at least two nucleotides.

* * * * *